US00PP10502P

United States Patent [19]

Lemon

[11] Patent Number: Plant 10,502

[45] Date of Patent: Jul. 14, 1998

[54] VARIETY OF GERANIUM PLANT NAMED 'ELYANE'

[75] Inventor: David Lemon, Lompoc, Calif.

[73] Assignee: John Bodger & Sons Company, So. El Monte, Calif.

[21] Appl. No.: 724,709

[22] Filed: Oct. 1, 1996

[51] Int. Cl.[6] ..... A01H 5/00

[52] U.S. Cl. ..... Plt./87.12

[58] Field of Search ..... Plt./87.12

[56] References Cited

U.S. PATENT DOCUMENTS

P.P. 7,271 7/1990 Guillou et al. ..... Plt./87.12

P.P. 7,358 10/1990 Guillou et al. ..... Plt./87.12

*Primary Examiner*—Howard J. Locker

*Attorney, Agent, or Firm*—Fulwider Patton Lee & Utecht, LLP

[57] ABSTRACT

The cultivar is characterized by its medium green zoned foliage and deep red velvet bloom. Its improved rooting ability and continuous, prolific flowering provide excellent cuttings and for quick recovery following wet weather conditions. The blooms are slow to shatter and exhibit excellent post-harvest quality.

2 Drawing Sheets

BACKGROUND OF THE NEW PLANT

The present invention comprises a new and distinct cultivar of *Pelargonium×peltatum* known by the varietal name Elyane (Oglevee No. 3177, Bodger No. 3GM 9-8). The new variety was discovered in a selective breeding program by David Lemon at Bodger Seeds, Ltd., Lompoc, Calif. The new variety is a selection from the crossing of Nicole (U.S. Plant Pat. No. 7,358) which is characterized by a medium pink flower having burgundy markings, with Romy (Bodger No. 1 GM 308 unpatented) which has dark red flowers as distinguished by the claimed cultivar which has a deep red velvet bloom over medium green foliage.

The new cultivar was first asexually reproduced by cuttings at Oglevee Ltd., Connellsville, Pa., and has been repeatedly asexually reproduced by cuttings at Oglevee Ltd. in Connellsville, Pa. It has been found to retain its distinctive characteristics through successive propagations.

The new cultivar, when grown in a glass greenhouse in Connellsville, Pa., using full light, 60° Fahrenheit night temperature, 68° Fahrenheit day temperature, 72° Fahrenheit vent temperature and grown in a soilless media of constant fertilizer 200–250 parts per million of nitrogen and potassium has a response time of six weeks from the rooted cutting to a flowering plant in a 10.0 cm pot.

DESCRIPTION OF THE DRAWINGS

The accompanying drawings illustrate the new cultivar, the colors depicted being as nearly true as possible with color illustrations of this type.

Sheet 1 represents a side view of the new cultivar, showing the bloom, foliage and growth habit.

Sheet 2 shows the bloom in greater detail.

DESCRIPTION OF THE NEW PLANT

The following detailed description sets forth characteristics of the new cultivar. The data which defines each characteristic was collected from asexual reproductions carried out by Oglevee Ltd. in Connellsville, Pa. The plant histories were taken on rooted cuttings believed to have been potted on approximately Feb. 1, 1996 and flowering on approximately Mar. 14, 1996 under full light and greenhouse, and colorings were taken indoors under 200–220 foot candles of fluorescent cool white light using The R.H.S. Colour Chart of The Royal Horticultural Society of London.

The Plant

Classification:

*Botanical.*—*Pelargonium×peltatum.*

*Commercial.*—Ivy Geranium Elyane.

Form: Cascading mound.

*Height.*—21 cm–25.5 cm from media.

*Growth.*—Free branching; free and early flowering; upright mound with cascading side growth.

*Strength.*—Holds an upright mound shape without artificial support while allowing outer shoots to cascade.

Foliage: Reflective; non-pubescent; stalked leaf attachment.

Leaves:

*Size.*—9.3 cm–10.2 cm.

*Shape.*—Reniform with cordate base.

*Margin.*—Crenately lobed.

*Texture.*—Smooth, leathery.

*Color.*—Green Group 137A. Bottom: Green group 137C. Zone: Greyed-Purple Group 187B.

*Ribs and veins.*—Palmate venation: Color: Yellow-Green Group 146D.

Petioles:

*Length.*—7–12 cm in length.

*Color.*—Yellow-Green Group 146D.

Stem:

*Color.*—Yellow-Green Group 146D.

*Internodes.*—4 cm–7.5 cm in length.

The Bud (Umbel)

Shape: Elliptical cluster.

Size: 1.9 cm–3.0 cm.

Inflorescence

Blooming habit: Free and early flowering, continuous.

Borne: Florets on pedicel; pedicel on peduncle.

Close florets:

*Bud size.*—Just cracking color; 0.6–0.9 cm×1.2–1.4 cm.

Size:

*Fully open bloom.*—9–11 cm across.

Open florets:

*Form.*—Slight cupped; some are flattened-semidouble; about 11 florets appearing per inflorescence.

*Color.*—Top: Red Group 46A at margins; Red Group 46B at centers, veining is Red Group 53A. Bottom: Red Group 46 D with veining of Red Group 46A. Eye: None.

*Petals.*—13–19 in number, margin entire, separate, not united.

*Size.*—5.5–5.8 cm across.

*Texture and appearance.*—Velvety; appearance from a distance is a deep red velvet bloom above medium green zoned foliage.

Petaloids:

*Quantity.*—4–14 in number.

*Shape.*—Irregular narrow, twisted and curled; some "forked".

*Color.*—Top: Red Group 46B. Bottom: Red Group 46D.

Pedicel:

*Length.*—2.9–3.8 cm.

*Color.*—At peduncle end Yellow -Green Group 146D with Greyed-Purple Group 187D at floret end.

Peduncle:

*Length.*—12–18 cm.

*Color.*—Yellow-Green Group 146D.

Persistence:

*Disease resistance.*—Not known.

*Lasting quality.*—Less shattering than current market variety 'Simone'.

Reproductive Organs

Stamens:

*Anthers.*—Length: 0.3 cm.

*Filaments.*—Length: 0.7–1.1 cm. Color: White.

*Pollen.*—Brown to golden brown.

Pistils:

*Number.*—One.

*Length.*—1.3–1.6 cm.

*Stigma.*—Color: Maroon — red with white basal section; 5 parted.

*Style.*—Length: 0.7–0.9 cm (fully "ripened" floret).

Ovaries:

*Color.*—Green, pubescent, superior.

*Length.*—5 mm.

Fruit: None.

General Characteristics

Elyane is an improvement over the current variety Simone (U.S. Plant Pat. No. 7,271) which is characterized by a rich red color flower over medium green foliage having a very faint zone while Elyane is characterized by having a distinct zone and by having improved qualities of post harvest (less shattering). Elyane is an excellent cutting producer and exhibits a controlled growth habit for the grower but will grow into a trailing basket for the consumer.

I claim:

1. A new and distinct variety of Geranium plant, substantially as shown and described.

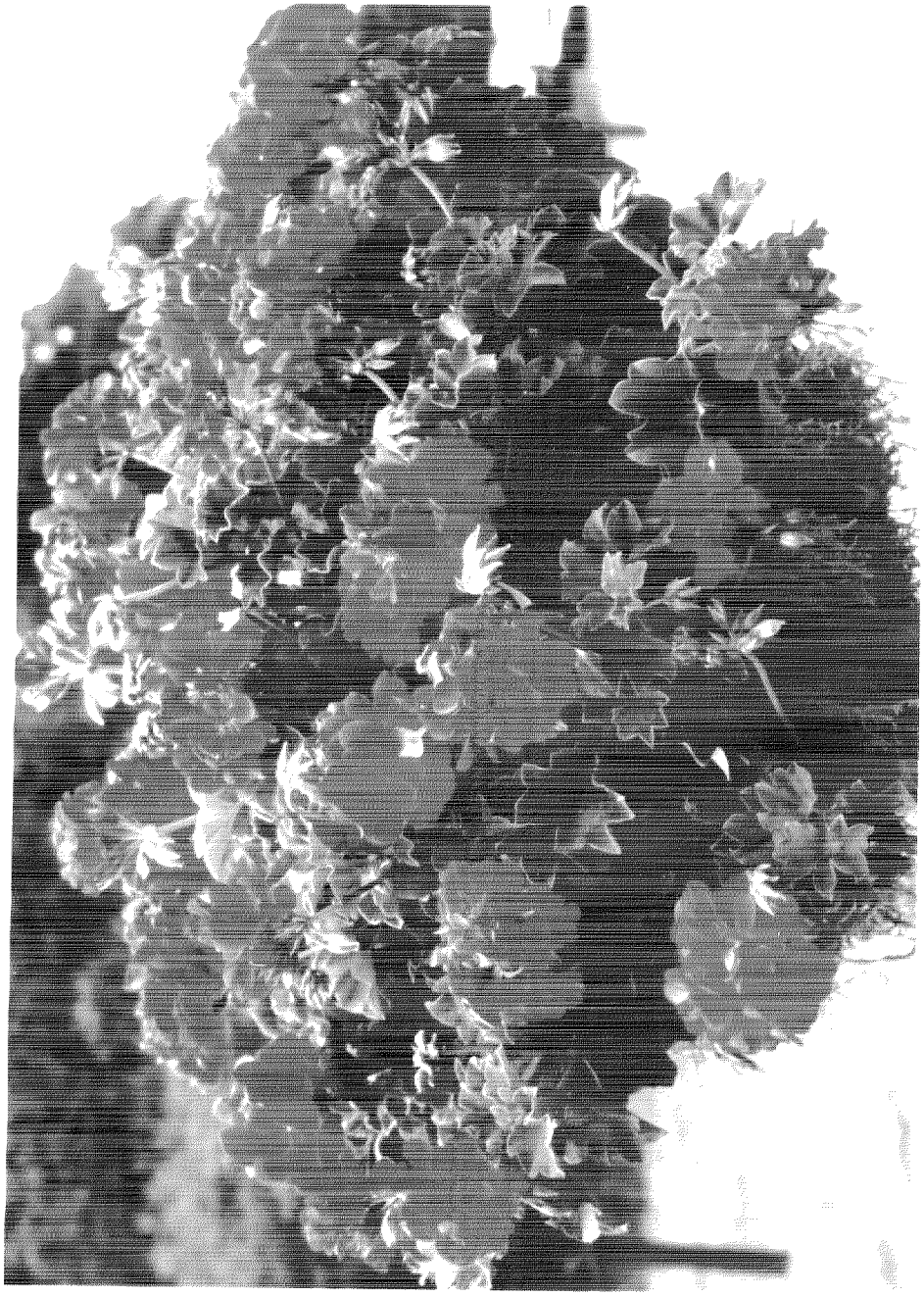

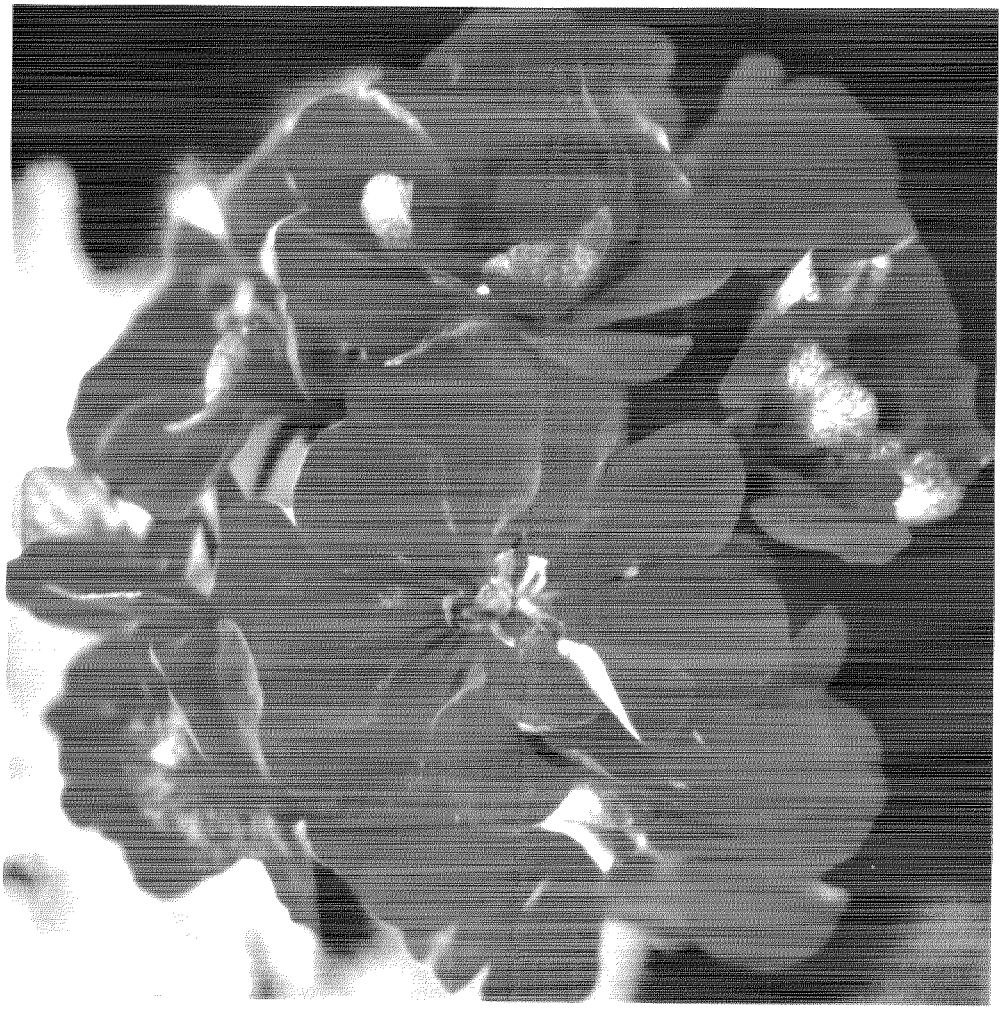

* * * * *